US006800769B2

(12) United States Patent
Stutz et al.

(10) Patent No.: US 6,800,769 B2
(45) Date of Patent: Oct. 5, 2004

(54) PROCESS FOR THE PREPARATION OF SUBSTITUTED OCTANOYL AMIDES

(75) Inventors: Stefan Stutz, Basel (CH); Peter Herold, Basel (CH)

(73) Assignee: Speedel Pharma AG, Basel (CH)

( * ) Notice: Subject to any disclaimer, the term of this patent is extended or adjusted under 35 U.S.C. 154(b) by 0 days.

(21) Appl. No.: 10/333,847

(22) PCT Filed: Jun. 26, 2001

(86) PCT No.: PCT/CH01/00400

§ 371 (c)(1),
(2), (4) Date: Jan. 24, 2003

(87) PCT Pub. No.: WO02/08172

PCT Pub. Date: Jan. 31, 2002

(65) Prior Publication Data

US 2003/0181765 A1 Sep. 25, 2003

(30) Foreign Application Priority Data

Jul. 25, 2000 (CH) .............................................. 1464/00

(51) Int. Cl.$^7$ ........................................... C07C 247/06
(52) U.S. Cl. ............................. 552/11; 554/36; 554/51; 554/62
(58) Field of Search ............................. 552/11; 554/36, 554/51, 62

(56) References Cited

U.S. PATENT DOCUMENTS 5,559,111 A * 9/1996 Goschke et al. ........ 514/227.5

FOREIGN PATENT DOCUMENTS

| EP | 0 678 500 A | 10/1995 |
|----|-------------|---------|
| EP | 0 678 503 A | 10/1995 |
| EP | 0 678 514 A | 10/1995 |

OTHER PUBLICATIONS

Peter Herold et al., "A Versatile and Stereocontrolled Synthesis of Hydroxyethylene Dipeptide Isosters", Journal of Organic Chemistry, American Chemical Society. Easton, US vol. 54, No. 5, Mar. 3, 1989, pp. 1178–1185.

* cited by examiner

*Primary Examiner*—Shailendra Kumar
(74) *Attorney, Agent, or Firm*—Wenderoth, Lind & Ponack, L.L.P.

(57) ABSTRACT

Compounds of formula (XII), are simultaneously halogenated in the 5 position and hydroxylated in the 4 position under lactonization, the halolactone is reacted with an amine to form a carboxamide, the halogen is replaced with azide, if necessary after the introduction of a hydroxy protecting group, the resulting azide is converted to a lactone, the lactone is amidated and then the azide converted to the amine group, in order to obtain compounds of formula (I) or a salt thereof.

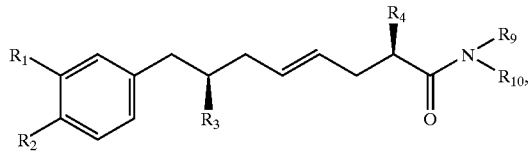

(XII)

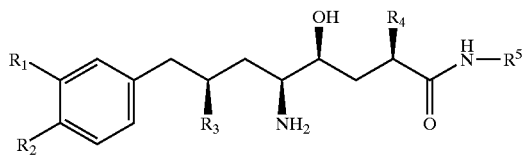

(I)

2 Claims, No Drawings

PROCESS FOR THE PREPARATION OF SUBSTITUTED OCTANOYL AMIDES

This application is a 371 of PCT/CH01/00400, filed Jun. 26, 2001.

The invention relates to a stereospecific method for the preparation of 2(S),4(S),5(S),7(S)-2,7-dialkyl-4-hydroxy-5-amino-8-aryloctanoyl amides and their physiologically acceptable salts; and new compounds used as intermediates in the multistage process.

In EP-A-0 678 503, δ-amino-γ-hydroxy-ω-aryl-alkanecarbox-amides are described, which exhibit renin-inhibiting properties and could be used as antihypertensive agents in pharmaceutical preparations. The manufacturing procedures described are unsatisfactory in terms of the number of process steps and yields and are not suitable for an industrial process. A disadvantage of these processes is also that the total yields of pure diastereomers that are obtainable are too small.

It has now been surprisingly found that these alkanecarboxamides can be prepared both in high total yields and in a high degree of purity, and that selectively pure diastereomers are obtainable, if the double bond of 2,7-dialkyl-8-aryl-4-octenic acid amides is simultaneously halogenated in the 5 position and hydroxylated in the 4 position under lactonization, the lactone ring is opened with an amine during the formation of the carboxamide, then the hydroxy group is replaced with azide, if necessary after protection of the hydroxy group, the resulting compound is lactonized, the lactone amidated and then the azide group converted to the amine group.

A first object of the invention is a process for the preparation of compounds of formula I and their physiologically acceptable salts,

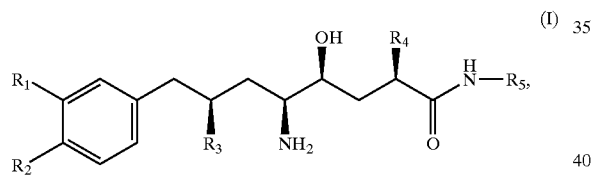
(I)

wherein
  R$_1$ and R$_2$ are, independently of one another, H, C$_1$–C$_6$alkyl, C$_1$–C$_6$halogenalkyl, C$_1$–C$_6$alkoxy, C$_1$–C$_6$alkoxy-C$_1$–C$_6$alkyl, or C$_1$–C$_6$alkoxy-C$_1$–C$_6$alkyloxy, R$_3$ is C$_1$–C$_6$alkyl, R$_4$ is C$_1$–C$_6$alkyl, and R$_5$ is C$_1$–C$_6$alkyl, C$_1$–C$_6$hydroxyalkyl, C$_1$–C$_6$alkoxy-C$_1$–C$_6$-alkyl, C$_1$–C$_6$alkanoyloxy-C$_1$–C$_6$alkyl, C$_1$–C$_6$aminoalkyl, C$_1$–C$_6$alkylamino-C$_1$–C$_6$-alkyl, C$_1$–C$_6$-dialkylamino-C$_1$–C$_6$-alkyl, C$_1$–C$_6$-alkanoyl-amido-C$_1$–C$_6$-alkyl, HO(O)C—C$_1$–C$_6$-alkyl, C$_1$–C$_6$alkyl-O—(O)C—C$_1$–C$_6$alkyl, H$_2$N—C(O)—C$_1$–C$_6$alkyl, C$_1$–C$_6$alkyl-HN—C(O)C—C$_6$alkyl or (C$_1$–C$_6$alkyl)$_2$N—C(O)—C$_1$–C$_6$-alkyl, comprising the steps
a) reaction of a compound of formula II,

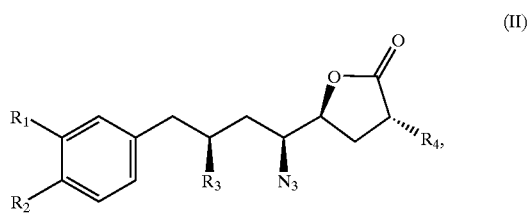
(II)

with an amine of formula R$_5$—NH$_2$ to form a compound of formula III,

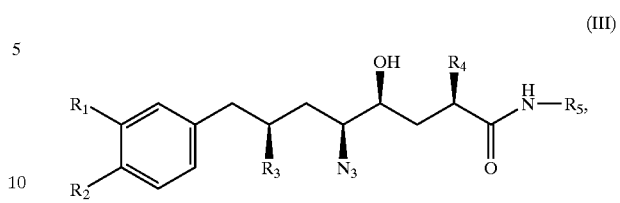
(III)

and
b) reduction of the azide group of the compound of formula III to the amine group and isolation of the compounds of formula I, if necessary with the addition of a salt-forming acid, comprising the preparation of the compound of formula II by reacting
c) a compound of formula IV

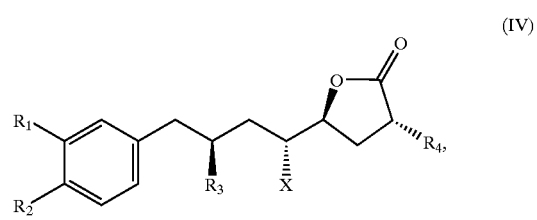
(IV)

wherein X is Cl, Br or I, with an amine to form a carboxamide of formula V,

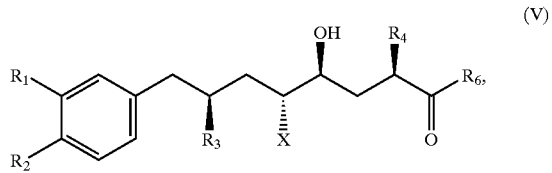
(V)

wherein R$_6$ is an amino group,
  d1) azidating a compound of formula V to form a compound of formula VI

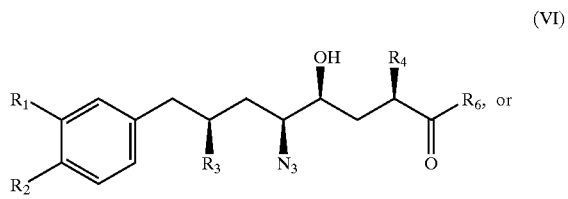
(VI)

d2) protecting the hydroxyl group in the compounds of formula V, and azidating the resulting compound of formula VII

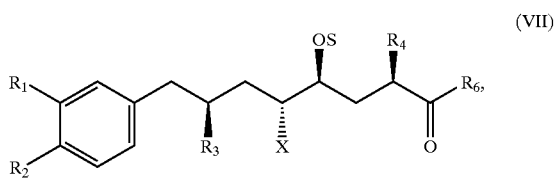
(VII)

wherein S is a protecting group, to form a compound of formula VIII,

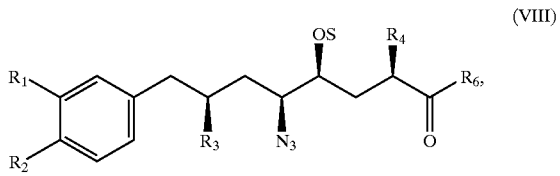

(VIII)

e) and then lactonizing the compound of formula VI or VIII in the presence of an acid to form a compound of formula II.

As an alkyl, $R_1$ and $R_2$ may be linear or branched and preferably comprise 1 to 4 C atoms. Examples are methyl, ethyl, n- and i-propyl, n-, i- and t-butyl, pentyl and hexyl.

As a halogenalkyl, $R_1$ and $R_2$ may be linear or branched and preferably comprise 1 to 4 C atoms, especially 1 or 2 C atoms. Examples are fluoromethyl, difluoromethyl, trifluoromethyl, chloromethyl, dichloromethyl, trichloromethyl, 2-chloroethyl and 2,2,2-trifluoroethyl.

As an alkoxy, $R_1$ and $R_2$ may be linear or branched and preferably comprise 1 to 4 C atoms. Examples are methoxy, ethoxy, n- and i-propyloxy, n-, i- and t-butyloxy, pentyloxy and hexyloxy.

As an alkoxyalkyl, $R_1$ and $R_2$ may be linear or branched. The alkoxy group preferably comprises 1 to 4 and especially 1 or 2 C atoms, and the alkyl group preferably comprises 1 to 4 C atoms. Examples are methoxymethyl, 1-methoxyeth-2-yl, 1-methoxyprop-3-yl, 1-methoxybut-4-yl, methoxypentyl, methoxyhexyl, ethoxymethyl, 1-ethoxyeth-2-yl, 1-ethoxyprop-3-yl, 1-ethoxybut-4-yl, ethoxypentyl, ethoxyhexyl, propyloxymethyl, butyloxymethyl, 1-propyloxyeth-2-yl and 1-butyloxyeth-2-yl.

As a $C_2-C_6$alkoxy-$C_1-C_6$alkyloxy, $R_1$ and $R_2$ may be linear or branched. The alkoxy group preferably comprises 1 to 4 and especially 1 or 2 C atoms, and the alkyloxy group preferably comprises 1 to 4 C atoms. Examples are methoxymethyloxy, 1-methoxyeth-2-yloxy, 1-methoxyprop-3-yloxy, 1-methoxybut-4-yloxy, methoxypentyloxy, methoxyhexyloxy, ethoxymethyloxy, 1-ethoxyeth-2-yloxy, 1-ethoxyprop-3-yloxy, 1-ethoxybut-4-yloxy, ethoxypentyloxy, ethoxyhexyloxy, propyloxymethyloxy, butyloxymethyloxy, 1-propyloxyeth-2-yloxy and 1-butyloxyeth-2-yloxy.

In a preferred embodiment, $R_1$ is methoxy- or ethoxy-$C_1-C_4$alkyloxy, and $R_2$ is preferably methoxy or ethoxy. Particularly preferred are compounds of formula I, wherein $R_1$ is 1-methoxyprop-3-yloxy and $R_2$ is methoxy.

As an alkyl, $R_3$ and $R_4$ may be linear or branched and preferably comprise 1 to 4 C atoms. Examples are methyl, ethyl, n- and i-propyl, n-, i- and t-butyl, pentyl and hexyl. In a preferred embodiment, $R_3$ and $R_4$ in compounds of formula I are in each case isopropyl.

As an alkyl, $R_5$ may be linear or branched and preferably comprise 1 to 4 C atoms. Examples of alkyl are listed hereinabove. Methyl, ethyl, n- and i-propyl, n-, i- and t-butyl are preferred.

As a $C_1-C_6$hydroxyalkyl, $R_5$ may be linear or branched and preferably comprise 2 to 6 C atoms. Some examples are 2-hydroxyethy-1-yl, 2-hydroxyprop-1-yl, 3-hydroxyprop-1-yl, 2-, 3- or 4-hydroxybut-1-yl, hydroxypentyl and hydroxyhexyl.

As a $C_1-C_6$alkoxy-$C_1-C_6$alkyl, $R_5$ may be linear or branched. The alkoxy group preferably comprises 1 to 4 C atoms and the alkyl group preferably 2 to 4 C atoms. Some examples are 2-methoxyethy-1-yl, 2-methoxyprop-1-yl, 3-methoxyprop-1-yl, 2-, 3- or 4-methoxybut-1-yl, 2-ethoxyethy-1-yl, 2-ethoxy-prop-1-yl, 3-ethoxyprop-1-yl, and 2-, 3- or 4-ethoxybut-1-yl.

As a $C_1-C_6$alkanoyloxy-$C_1-C_6$alkyl, $R_5$ may be linear or branched. The alkanoyloxy group preferably comprises 1 to 4 C atoms and the alkyl group preferably 2 to 4 C atoms. Some examples are formyloxymethyl, formyloxyethyl, acetyloxy-ethyl, propionyloxyethyl and butyroyloxyethyl.

As a $C_1-C_6$aminoalkyl, $R_5$ may be linear or branched and preferably comprise 2 to 4 C atoms. Some examples are 2-aminoethyl, 2- or 3-aminoprop-1-yl and 2-, 3- or 4-aminobut-1-yl.

As a $C_1-C_6$alkylamino-$C_1-C_6$alkyl and $C_1-C_6$dialkylamino-$C_1-C_6$-alkyl, $R_5$ may be linear or branched. The alkylamino group preferably comprises $C_1-C_4$alkyl groups and the alkyl group preferably 2 to 4 C atoms. Some examples are 2-methylaminoeth-1-yl, 2-dimethylaminoeth-1-yl, 2-ethylamino-eth-1-yl, 2-ethylaminoeth-1-yl, 3-methylaminoprop-1-yl, 3-dimethylaminoprop-1-yl, 4-methylaminobut-1-yl and 4-dimethylaminobut-1-yl.

As a $C_1-C_6$alkanoylamido-$C_1-C_6$alkyl, $R_5$ may be linear or branched. The alkanoyl group preferably comprises 1 to 4 C atoms and the alkyl group preferably 1 to 4 C atoms. Some examples are 2-formamidoeth-1-yl, 2-acetamidoeth-1-yl, 3-propionylamidoeth-1-yl and 4-butyroylamidoeth-1-yl.

As a HO(O)C—$C_1-C_6$-alkyl, $R_5$ may be linear or branched, and the alkyl group preferably comprises 2 to 4 C atoms. Some examples are carboxymethyl, carboxyethyl, carboxypropyl and carboxybutyl.

As a $C_1-C_6$-alkyl-O—(O)C—$C_1-C_6$alkyl, $R_5$ may be linear or branched, and the alkyl groups preferably comprise independently of one another 1 to 4 C atoms. Some examples are methoxycarbonylmethyl, 2-methoxycarbonyleth-1-yl, 3-methoxycarbonylprop-1-yl, 4-methoxycarbonylbut-1-yl, ethoxy-carbonylmethyl, 2-ethoxycarbonyleth-1-yl, 3-ethoxycarbonyl-prop-1-yl, and 4-ethoxycarbonylbut-1-yl.

As a $H_2N$—C(O)—$C_1-C_6$alkyl, $R_5$ may be linear or branched, and the alkyl group preferably comprises 2 to 6 C atoms. Some examples are carbamidomethyl, 2-carbamidoeth-1-yl, 2-carbamido-2,2-dimethyleth-1-yl, 2- or 3-carbamidoprop-1-yl, 2-, 3- or 4-carbamidobut-1-yl, 3-carbamido-2-methylprop-1-yl, 3-carbamido-1,2-dimethylprop-1-yl, 3-carbamido-3-methyl-prop-1-yl, 3-dicarbamido-2,2-dimethylprop-1-yl, 2-, 3-, 4- or 5-carbamidopent-1-yl, 4-carbamido-3, 3- or -2,2-dimethylbut-1-yl.

As a $C_1-C_6$alkyl-HN—C(O)—$C_1-C_6$-alkyl or $(C_1-C_6$alkyl$)_2$N—C(O)—$C_1-C_6$-alkyl, $R_5$ may be linear or branched, and the NH-alkyl group preferably -comprises 1 to 4 C atoms and the alkyl group preferably 2 to 6 C atoms. Examples are the carbamidoalkyl groups defined hereinabove, whose N atom is substituted with one or two methyl, ethyl, propyl or butyl.

A preferred subgroup of compounds of formula I is that in which $R_1$ is $C_1-C_4$alkoxy or $C_1-C_4$alkoxy-$C_1-C_4$alkyloxy, $R_2$ is $C_1-C_4$alkoxy, $R_3$ is $C_1-C_4$alkyl, $R_4$ is $C_1-C_4$alkyl and $R_5$ is $H_2NC(O)$—$C_1-C_6$alkyl which if necessary is N-monosubstituted or N-di-$C_1-C_4$alkyl substituted.

A more preferred subgroup of compounds of formula I is that in which $R_1$ is methoxy-$C_2-C_4$-alkyloxy, $R_2$ is methoxy or ethoxy, $R_3$ is $C_2-C_4$alkyl, $R_4$ is $C_2-C_4$alkyl and $R_5$ is $H_2NC(O)$—$C_1-C_6$alkyl.

An especially preferred compound of formula I is that in which $R_1$ is 3-methoxy-prop-3-yloxy, $R_2$ is methoxy, $R_3$ and $R_4$ are 1-methyleth-1-yl, and $R_5$ is $H_2NC(O)$-[$C(CH_3)_2$]—$CH_2$—.

As an amino group, $R_6$ may be —$NH_2$, primary and preferably secondary amino, the amino groups comprising 1 to 20 C atoms and preferably 2 to 12. The amino group preferably corresponds to the formula —$N(R_7)_2$, wherein $R_7$ is $C_1$–$C_4$alkyl, cyclopentyl, cyclohexyl, phenyl or benzyl, or both $R_7$ are together tetramethylene, pentamethylene or 3-oxapentylene. Preferred examples of $R_7$ are methyl, ethyl, n-propyl and n-butyl.

Protecting group S in the compounds of formulae VII and VIII are preferably acyl groups, which may comprise 1 to 12 and preferably 1 to 8 C atoms. Some examples are formyl, acetyl, propionyl and butyroyl. Acetyl is especially preferred.

The individual process steps may be carried out in the presence of solvent. Suitable solvents are water and organic solvents, especially polar organic solvents, which can also be used as mixtures of at least two solvents. Examples of solvents are hydrocarbons (petroleum ether, pentane, hexane, cyclohexane, methylcyclohexane, benzene, toluene, xylene), halogenated hydrocarbon (dichloromethane, chloroform, tetrachloroethane, chlorobenzene); ether (diethyl ether, dibutyl ether, tetrahydrofuran, dioxane, ethylene glycol dimethyl or diethyl ether); carbonic esters and lactones (methyl acetate, ethyl acetate, methyl propionate, valerolactone); N,N-substituted carboxamides and lactams (dimethylformamide, dimethylacetamide, N-methylpyrrolidone); ketones (acetone, methylisobutylketone, cyclohexanone); sulfoxides and sulfones (dimethylsulfoxide, dimethylsulfone, tetramethylene sulfone); alcohols (methanol, ethanol, n- or i-propanol, n-, i- or t-butanol, pentanol, hexanol, cyclohexanol, cyclohexanediol, hydroxymethyl or dihydroxy-methyl cyclohexane, benzyl alcohol, ethylene glycol, diethylene glycol, propanediol, butanediol, ethylene glycol monomethyl or monoethyl ether, and diethylene glycol monomethyl or monoethyl ether; nitriles (acetonitrile, propionitrile); tertiary amines (trimethylamine, triethyl-amine, tripropylamine and tributylamine, pyridine, N-methyl-pyrrolidine, N-methylpiperazine, N-methylmorpholine) and organic acids (acetic acid, formic acid).

Process Step a)

The reaction of compounds of formula II with a compound $R_5NH_2$ by opening of the lactone ring to form compounds of formula III is expediently carried out in the presence of alcohols or amines which are capable of forming activated carbonic esters or carboxamides. Such compounds are well-known. They may be 2-hydroxypyridine, N-hydroxycarboxamides and imides, and carboximides (N-hydroxysuccinimide). Organic solvents are used as solvent, tertiary amines being of advantage, for example trimethylamine or triethylamine. The reaction temperature may range for example from approximately 40° C. to 150° C. and preferably from 50° C. to 120° C.

Process Step b)

Reduction of the azide group to the amine group in the compounds of formula III takes place in a manner known per se (see Chemical Reviews, Vol. 88 (1988), pages 298 to 317), for example using metal hydrides or more expediently using a catalytic method with hydrogen in the presence of homogeneous (Wilkinson catalyst) or heterogeneous catalysts, for example Raney nickel or precious metal catalysts such as platinum or palladium, if necessary on substrates such as carbon. The hydrogenation can also be carried out if necessary catalytically under phase transfer conditions, for example with ammonium formate as hydrogen donor. It is of advantage to use organic solvents. The reaction temperature may range for example from approximately 0° C. to 200° C. and preferably from 10° C. to 100° C. Hydrogenation may be carried out at normal pressure or increased pressure up to 100 bar, for example, and preferably up to 50 bar.

The compounds of formula I may be converted to addition salts in a manner known per se by treatment with monobasic or polybasic, inorganic or organic acids. Hemifumarates are preferred.

Process Step c)

The reaction of the halolactone with an amine to form carboxamide is advantageously carried out in organic solvents such as halogenated hydrocarbons (chloroform, dichloromethane). The reaction temperature may range for example from approximately –30° C. to 80° C. and preferably from –20° C. to 50° C. The amine is expediently used as a salt, for example as a halogenide. Dimethyl ammonium chloride is preferably used. The reaction is preferably carried out in the presence of at least equimolar quantities of an alkyl aluminium halogenide such as dialkyl aluminium chloride (dimethyl or diethyl aluminium chloride). After hydrolytic treatment, the carboxamide can be isolated by means of extraction and purified by means of chromatography. The stereoselectivity is high and the yield can be as much as 70% or more.

Process Step d1)

Halogen X may be directly substituted with azide in the carboxamide of formula V obtained as described in step c). Suitable azidation agents are for example metal azides, especially alkaline earth metal azides and alkali metal azides, as well as silyl azides. Especially preferred azidation agents are lithium azide, sodium azide and potassium azide. The reaction may be carried out in organic solvents, for example N-alkylated lactams such as N-methylpyrrolidone or 1,3-dimethyl-3,4,5,6-tetrahydro-2(1H)-pyrimidone (DMPU). The reaction temperature may range for example from approximately 20° C. to 150° C. and preferably from 20° C. to 120° C. It may be expedient to include the use of phase; transfer catalysts. In the broader sense it is advantageous to carry out the reaction in the presence of preferably at least equimolar quantities of a base, especially tertiary amines. These tertiary amines may serve at the same time as solvents. The preparation and synthetic use of azides are described for example by E. F. V. Scriven in Chemical Reviews, Vol. 88 (1988), pages 298 to 317. As a result of secondary reactions due to the absence of the hydroxyl group, the yield in the non-optimized reaction is not very high and may be about 30% or more.

Process Step d2)

It has therefore proved very advantageous to protect the hydroxyl group against azidation in the compounds of formula VI, preferably with acyl groups. To this end, compounds of formula V are reacted with acylation agents, for example carboxylic acid anhydrides such as acetic acid anhydride or carboxylic acid halogenides such as acetylchloride. The reaction may be carried out with or without solvents. The reaction temperature may be –20 to 80° C. The reaction is expediently carried out in the presence of bases, for example tertiary amines. Examples of tertiary amines are trialkylamines (trimethylamine, triethylamine), N-alkylated cyclic amines (N-alkylpyrrolidine), dialkylaminopyridines (dimethylaminopyridine) and pyridine. After hydrolytic treatment, the protected carboxamide can be isolated by means of extraction and purified by means of chromatography. The yield is generally more than 90%.

Azidation may then be carried out as described in process step d1). The yields are substantially higher than with direct azidation as described in process step d1) and are more than 75% in the non-optimized process step d2)

Process Step e)

Lactonization of compounds of formula VI or VIII to form compounds of formula II is expediently carried out at a temperature of −20 to 100° C. and in the presence of a solvent such as alcohols (methanol, ethanol or propanol) or hydrocarbons (benzene, toluene or xylene). Inorganic acids and advantageously organic acids are used, especially mineral acids such as hydrochloric acid, hydrobromic acid or sulfuric acid, sulfonic acids and carboxylic acids. The azidolactone of formula II may be isolated for example by extraction with organic solvents. The desired stereoisomer is also formed in this step at high yields of up to 90% or more.

Some intermediates prepared using the process according to the invention are new and represent further objects of the invention.

A further object of the invention is thus a compound of formula IX,

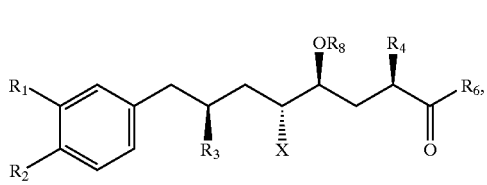

(IX)

wherein

X is halogen, $R_1$ and $R_2$ are, independently of one another, H, $C_1$–$C_6$alkyl, $C_1$–$C_6$-halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, $R_6$ is an amino group, and $R_8$ is a protecting group or hydrogen.

A further object of the invention is a compound of formula IXa,

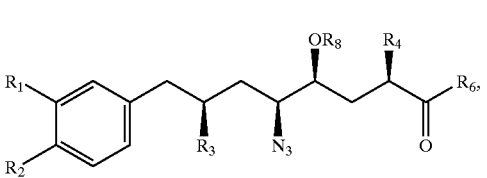

(IXa)

wherein $R_1$ and $R_2$ are, independently of one another, H, $C_2$–$C_6$alkyl, $C_1$–$C_6$-halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, $R_6$ is an amino group, and $R_8$ is a protecting group or hydrogen.

For residues X, $R_1$, $R_2$, $R_3$, $R_4$, $R_6$, and $R_8$ in compounds of formulae IX and IXa, the embodiments and preferences described hereinbefore apply.

The compounds of formula IV are obtainable by reacting in a first step a compound of formula X,

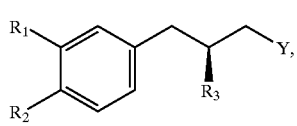

(X)

with a compound of formula IX,

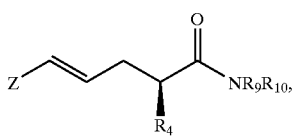

(XI)

wherein $R_1$ to $R_4$ are as defined hereinbefore, including the preferences, Y is Cl, Br or I and Z is Cl, Br or I (Y and Z are preferably Br and especially Cl), and $R_9$ is $C_1$–$C_6$alkyl, $R_{10}$ is $C_1$–$C_6$-akyl or $C_1$–$C_6$alkoxy, or $R_9$ and $R_{10}$ are together tetramethylene, pentamethylene, 3-oxa-1,5-pentylene or —$CH_2CH_2O$—$C(O)$— substituted if necessary with $C_1$–$C_4$alkyl, phenyl or benzyl, in the presence of an alkali or alkaline earth metal to form a compound of formula XII,

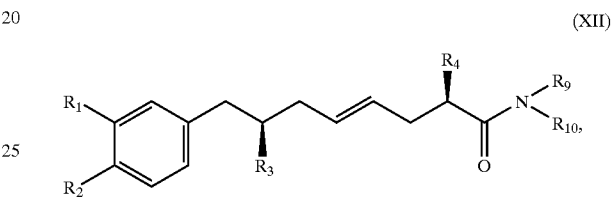

(XII)

wherein $R_9$ is $C_1$–$C_6$alkyl, $R_{10}$ is $C_1$–$C_6$alkyl or $C_1$–$C_6$alkoxy, or $R_9$ and $R_{10}$ together are tetramethylene, pentamethylene, 3-oxa-1,5-pentylene or —$CH_2CH_2O$—$C(O)$— substituted if necessary with $C_1$–$C_4$alkyl, phenyl or benzyl.

As an alkyl, $R_9$ and $R_{10}$ in formula XII may be branched and preferably linear and are preferably $C_1$–$C_4$alkyl, for example methyl or ethyl. $R_{10}$ as alkoxy may preferably be linear and is preferably $C_1$–$C_4$alkoxy, for example methoxy or ethoxy. $R_9$ and $R_{10}$ together are preferably tetramethylene, —$CH_2CH_2$—$O$—$C(O)$— or —$CH(CH_2C_6H_5)$ $CH_2$—$O$—$C(O)$—.

The coupling of Grignard reagents with alkenyl halogenides in an ether such as, for example, tetrahydrofuran or dioxan as solvents in the presence of catalytic quantities of a soluble metal complex, for example an iron complex such as iron acetonyl acetate, and in the presence of more than equimolar quantities of a solvent stabilizing the metal complex, for example n-methylpyrrolidone, is described by G. Cahiez et al. in Synthesis (1998), pages 1199–1200. The reaction temperature may for example be −50 to 80° C., preferably −20 to 50° C. Catalytic quantities may for example be 0.1 to 20% by weight in relation to a compound of formula VII. It is expedient to carry out the reaction so that initially a compound of formula VI is converted to a Grignard compound (for example with magnesium) and then adding a solution of a compound of formula VII, metal complex and N-methylpyrrolidone, or vice versa.

It was found to be of advantage when only catalytic quantities of a solvent stabilizing the metal complexes, for example n-methylpyrrolidone, were used. Catalytic quantities may for example be 1 to 10 mol percent, preferably 1 to 5 mol percent, in relation to the compounds of formula XI or XII.

Compounds of formula X in the form of their racemates or enantiomers are known or capable of being prepared according to analogous Processes. For example, $R_1R_2$phenylaldehyde may be reacted with $R_3$diethoxyphosphorylacetic acid ester to form 2-$R_3$-3-($R_1R_2$phenyl)acrylic acid esters, these may then be hydrogenated to form the corresponding propionic acid esters, the ester group saponified and the carboxylic acid reduced to alcohol, and finally the hydroxyl group substituted with halogen. Enantiomers are obtainable by separating the racemates of the carboxylic acids with for example quinine or by enzymatic resolution of the racemates of the corresponding carboxylic acid esters. Details are described in the examples. A possible asymmetric synthesis of compounds of formula VI is described in EP-A-0 678 503.

Compounds of formula XI in the form of their racemates or enantiomers may be prepared by the reaction of metalled carbonic esters of formula $R_4CH_2COOR$ (for example lithium isovaleric acid esters) with trans-1,3-halogenpropene, then halogenation of the resulting carboxylic acid to form the acid halogenide and reaction with a secondary amine. The coupling of metalled carbonic esters with trans-1,3-halogenpropene can be carried out asymmetrically according to the method described by D. A. Evans in Asymmetric Synthesis, Vol. 3, 1984 (Academic Press Inc.), pages 2–110. Enantiomers are obtainable by separating the racemates of the carboxylic acids with for example cinchonidine or by enzymatic separation of the racemates of the corresponding carbonic esters.

In a second process step, compounds of formula XII are reacted with a halogenation agent in the presence of water and if necessary an acid to form a compound of formula IV.

Suitable chlorination, bromination and iodination agents are elemental bromine and iodine, in particular N-chloro, N-bromo and N-iodocarboxamides and dicarboximides. Preferred are N-chloro, N-bromo and N-iodophthalimide and especially chloro, N-bromo and N-iodosuccinimide, as well as tertiary butyl hypochlorite and N-halogenated sulfonamides and sulfonimides, for example chloramine T. It is of advantage to carry out the reaction in organic solvents. The reaction temperature may range for example from approximately −70° C. to ambient temperature and preferably from −30° C. to 10° C. Carboxamides are advantageously lactonized in the presence of inorganic or organic acids, at least equimolar quantities of water, and reacted in the presence of water-miscible solvents, for example tetrahydrofuran or dioxane. Suitable acids are for example formic acid, acetic acid, methanesulfonic acid, trifluoroacetic acid, trifluoro-methanesulfonic acid, toluenesulfonic acid, $H_2SO_4$, $H_3PO_4$, hydrogen halides, acid ion exchange resins, and acids immobilized on solid carriers. Water is generally used in at least equimolar quantities.

With the choice of lactones of formula IV, the compounds of formula I, which per se are complex compounds, can be prepared in a convergent and simple manner, which is especially true of these enantioselective or diastereoselective synthesis. The total yield from all process steps a) to e) may amount to 40% or more, which makes an industrial application feasible.

The following examples explain the invention in more detail.

A) Preparation of Compounds of Formula X (EP-A-0 678 503)

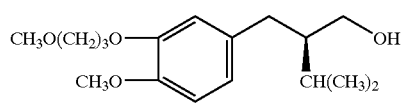

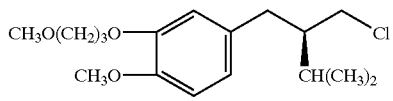

(A1)

EXAMPLE A1

An agitated solution of 174 g 2R-[4-methoxy-3-(3-methoxypropoxy)benzyl]-3-methylbutan-1-ol [EP 0 678 503] and 1.3 l carbon tetrachloride is cooled to 10° C. 393 ml trioctylphosphine is added dropwise, and the reaction solution is then stirred for 16 hours at ambient temperature. The mixture is completely concentrated by evaporation and the residue extracted between dichloromethane (3×) and water (1×). The combined organic phases are dried over magnesium sulfate, filtered and concentrated by evaporation. The residue is purified by means of flash chromatography ($SiO_2$ 60F/ethyl acetate/hexane 1:9), and title compound A5 is obtained after crystallization (hexane at −50° C.) as a white solid (152.3 g, 82%): melting point 51–52° C.; $^1$H-NMR (400 MHz, $CDCl_3$, δ): 1.0 (m, 6H), 1.71 (m, 1H), 1.93 (m, 1H), 2.12 (m, 2H), 2.35 (m, 1H), 2.77 (m, 1H), 3.39 (s, 3H), 3.40–3.55 (m, 2H), 3.71 (t, 2H), 3.87 (s, 3H), 4.13 (m, 3H), 6.65–6.85 (m, 3H) ppm.

B) Preparation of Compounds of Formula XI

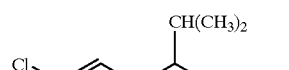

(B1)

(B2)

(B3)

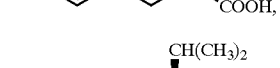

(B4)

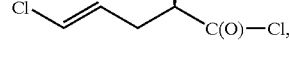

(B5)

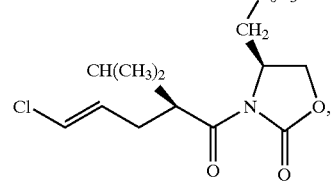

(B6)

EXAMPLE B1

An agitated solution of 24.9 ml diisopropylamine and 240 ml tetrahydrofuran is cooled to minus 15° C., and 100 ml 1.6 M n-butyl lithium solution (in hexane) is added over a period of 10 minutes. The solution is stirred for 30 minutes at −15° C. and then, over a period 30 minutes, a solution of 24.1 ml ethyl isovalerate in 80 ml tetrahydrofuran is added dropwise.

The mixture is stirred for a further 5 minutes at −15° C., and then 19.5 g trans-1,3-dichloropropene and 2.4 g sodium iodide are added consecutively. The reaction mixture is stirred for a further 16 hours at ambient temperature, and then 500 ml 10% aqueous ammonium chloride solution is added. The mixture is extracted with diethyl ether (3×) and the organic phases washed consecutively with water (1×), 0.1 M sodium thiosulfate solution (1×) and brine (1×). The combined organic phases are dried with sodium sulfate and concentrated by evaporation. By means of distillation, title compound B1 is obtained as a colourless oil (24.8 g, 76%) $^1$H-NMR (400 MHz, CDCl$_3$, δ): 0.95 (m, 6H), 1.30 (t, 3H), 1.92 (m, 1H), 2.20-2.40 (m, 3H), 4.20 (m, 2H), 5.80-6.10 (m, 2H) ppm.

EXAMPLE B2

A solution of 150.2 g B1, 500 ml ethanol and 500 ml 2N sodium hydroxide solution is stirred for 18 hours under reflux. The ethanol is evaporated from the reaction mixture, the aqueous solution acidified with 1N hydrochloric acid and extracted with diethyl ether (3×). The organic phases are dried over magnesium sulfate and concentrated by evaporation. By means of flash chromatography (SiO$_2$ 60F/dichloromethane/methanol 20:1), title compound B2 is obtained from the residue as a slightly orange oil (83.7 g, 65%): $^1$H-NMR (400 MHz, CDCl$_3$, δ): 1.03 (m, 6H), 1.98 (m, 1H), 2.20–2.45 (m, 3H), 5.80–6.10 (m, 2H) ppm.

EXAMPLE B3
Racemate Resolution of Compound B2

5.0 g B2, 5.0 g cinchonidine and 1.98 ml triethylamine are transferred to 150 ml tetrahydrofuran and stirred for 15 minutes under reflux. The oil bath is removed and the clear solution with a salt of B3 is inoculated with cinchonidine. Agitation is continued for 1 hour at ambient temperature and then for another 1 hour under ice cooling. The precipitate is filtered off, washed with twice 25 ml ice-cold acetone and then dried in a vacuum at 50° C. until constant weight is attained. 6.16 g (46.3%) of the enriched salt of B3 is obtained with cinchonidine; melting point 149° C. After double recrystallization from acetone, 4.20 g (31.6%) of the enriched salt of B3 is obtained with cinchonidine, melting point 155° C. The salt obtained in this way is distributed between 250 ml diethyl ether and 50 ml 1N HCl. The aqueous phase is separated off, the organic phase washed with saturated NaCl solution, dried over MgSO$_4$ and concentrated by evaporation in a vacuum. 1.58 g (31.6%) of enriched compound B3 is obtained as colourless oil.

EXAMPLE B4
Asymmetric Synthesis of B3 a) A solution of 290 g 4S-benzyl-3-(3-methyl-butyryl) oxazolidin-2-one in 0.58 l tetrahydrofuran is cooled to −78° C., and 1.14 l 1 M lithium hexamethyldisilazide (in tetrahydrofuran) is added dropwise over a period of 65 minutes. The mixture is stirred for another hour at −78° C., and a prepared solution of trans-1-chloro-3-iodopropene in tetrahydrofuran is then added. The temperature is allowed to increase to 0° C. and agitation is continued for a further 20 hours. 500 ml 10% ammonium chloride solution is added to the reaction mixture, which is then extracted with diethyl ether (2×1 l). The organic phases are washed with water (1×1 l), dried with sodium sulfate and concentrated by evaporation. By means of flash chromatography (SiO$_2$ 60F/ethyl acetate/hexane 5:1), title compound B5 is obtained from the residue as a slightly orange oil (582 g, 78%): $^1$H-NMR (400 MHz, CDCl$_3$, δ): 0.85 (m, 6H), 2.02(m, 1H), 2.3–2.55 (m, 2H), 2.75 (m, 1H), 3.30 (m, 1H), 3.88 (m,1H), 4.18 (m, 2H), 4.70 (m, 1H), 5.80–6.10 (m, 2H), 7.15–7.40 (m, 5H) ppm. Racemate resolution of compound A3 266.1 g sodium iodide is added to a solution of 184.7 g trans-1, 3-dichloropropene in 0.58 l tetrahydrofuran and the mixture stirred for 30 minutes under exclusion of light at ambient temperature. The mixture is filtered until clear and the filtrate used in the crude state.

b) To a solution of 155 g B4, 1.3 l tetrahydrofuran and 0.44 l water, stirred at 0° C., 315 ml 30% hydrogen peroxide solution is added dropwise over a period of 15 minutes. 22.1 g lithium hydroxide is added to the reaction mixture, then the cooling bath is removed and stirring is continued for 5 hours at 0–20° C. The reaction mixture is cooled again to 0° C., and a solution of 350 g sodium sulfite in 1.4 l water is added dropwise over a period of 30 minutes. The pH is adjusted to 9.8 by the addition of sodium hydrogencarbonate. The reaction mixture is filtered until clear and tetrahydrofuran evaporated from the filtrate. The aqueous solution obtained is washed with dichloromethane (3×3 l). The pH of the aqueous phase is adjusted to 3.0 with aqueous hydrochloric acid and then extracted with dichloromethane (3×2 l). The organic phases are dried over magnesium sulfate and concentrated by evaporation on a rotary evaporator. By means of distillation, title compound B3 is obtained from the residue as a colourless oil. (142 g, 87%). $^1$H-NMR (400 MHz, CDCl$_3$, δ): 1.02 (m, 6H), 1.98 (m, 1H), 2.25–2.45 (m, 3H), 5.85–6.10 (m, 2H) ppm.

EXAMPLE B4

4.42 ml oxalyl chloride is added to a solution of 4.54 g B3 in 25 ml toluene at ambient temperature. The reaction mixture is agitated for 15 minutes at ambient temperature, and then 0.052 ml N,N-dimethylformamide over a period of 1 minute. The reaction mixture is heated to reflux and agitated for 1 hour. The reaction solution is concentrated by evaporation and the residue distilled. Title compound B4 is obtained as a colourless oil. (4.43 g, 88%). $^1$H-NMR (400 MHz, CDCl3, δ): 1.02 (d, 3H), 1.08 (d, 3H), 2.16 (m, 1H), 2.40 (m, 1H), 2.45 (m, 1H), 2.68 (m,1H), 5.80–6.10 (m, 2H) ppm.

EXAMPLE B5

A solution of 1.53 g dimethylamine, 3.66 ml pyridine and 25 ml dichloromethane is cooled to 0° C., and then 4.42 g B5 in 25 ml dichloromethane is added dropwise at 0 to −10° C. The reaction mixture is stirred for a further 2 hours at 0° C. and then concentrated by evaporation on the Rotavapor. The residue is distributed between diethyl ether (2×) and 2N hydrochloric acid (3×), saturated sodium hydrogencarbonate solution (1×) and saturated saline solution. The organic fractions are combined, dried over sodium sulfate and concentrated. The residue is distilled, and title compound B6 is obtained as a colourless oil. (4.13 g, 89%). $[α]^{25}_D$-7,3 (c 1, chloroform). $^1$H-NMR (400 MHz, CDCl$_3$, δ): 0.90 (d, 3H), 0.95 (d, 3H), 1.92 (m, 1H), 2.20–2.30 (m, 1H), 2.35–2.50 (m, 2H), 2.98 (s,3H), 3.04 (s, 3H), 5.80–6.10 (m, 2H) ppm.

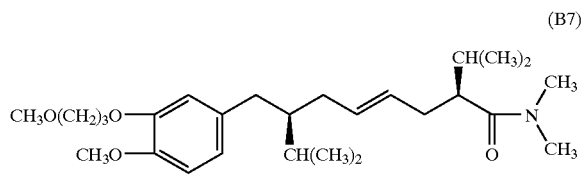

(B7)

EXAMPLE B6

A mixture of 10.7 g magnesium powder and 120 ml tetrahydrofuran is heated to 60° C., and 0.74 ml 1,2-dibromoethane then added over a period of 2 minutes (visible exothermic reaction). A solution of 34.6 g A1, 4.0 ml 1,2-dibromoethane and 320 ml tetrahydrofuran is added dropwise over a period of 15 minutes at 62–64° C. The mixture is stirred for another 30 minutes under reflux and then cooled down to ambient temperature. The reaction mixture is filtered under argon until clear and the resulting Grignard solution added dropwise over a period of 10 minutes to a solution of 20.4 g B6, 0.240 ml N-methylpyrrolidone, 0.88 g iron(III) acetylacetonate in 200 ml tetrahydrofuran at −5 to 0° C. The reaction mixture is agitated for a further 15 minutes at 0 to 10° C., and 320 ml 2N hydrochloric acid is then added. The mixture is now extracted with diethyl ether (3×500 ml) and the organic phases washed consecutively with water (1×400 ml) and saturated aqueous sodium chloride solution (1×400 ml). The combined organic phases are dried over sodium sulfate, filtered and concentrated on a rotary evaporator. By means of flash chromatography (SiO$_2$ 60F/diethyl ether/hexane 2:1), title compound B7 is obtained from the residue as a slightly yellowish oil (36.2 g, 81%): TLC R$_f$=0.09 (diethyl ether/hexane 2:1); $^1$H-NMR (500 MHz, CDCl$_3$, c : 0.82–0.99 (m, 12H), 1.49 (m, 1H), 1.69 (m, 1H), 1.78–1.98 (m, 3H), 2.10 (m, 2H), 2.17–2.41 (m, 5H), 2.92 (s, 3H), 3.0 (s, 3H), 3.37 (s, 3H), 3.58 (t, 2H), 3.84 (s, 3H), 4.10 (t, 2H), 5.26–5.34 (m, 1H), 5.36–5.44 (m, 1H), 6.64 (m, 2H), 6.78 (d, 1H) ppm.

C) Preparation of Compounds of Formula IV

EXAMPLE C1

Preparation of

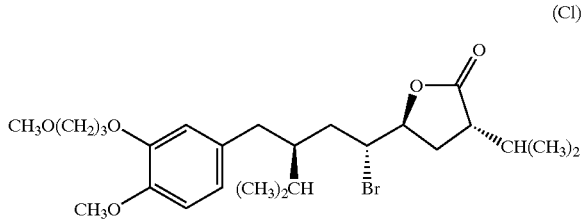

(C1)

3.85 ml water is added to a solution of 34.2 g B7 and 385 ml tetrahydrofuran, and the mixture cooled to 0° C. while being stirred. Then 10 times 1.03 ml 42.5% o-phosphoric acid and times 1.5 g N-bromosuccinimide are added alternately every 3 minutes. The reaction mixture is agitated for another 90 minutes at 0° C. and then, over a period of 10 minutes, is introduced to 600 ml sodium hydrogen sulfite solution cooled to 0° C. The mixture is agitated for another minutes at 0° C. and then extracted with diethyl ether (1×1 l and 2×0.5 l) The organic phases are washed consecutively with 1N hydrochloric acid (1×0.6 l), water (1×0.6 l), saturated aqueous sodium hydrogencarbonate solution (1×0.6 l) and brine (1×0.6 l), dried over sodium sulfate and concentrated by evaporation on a rotary evaporator. By crystallization (diisopropyl ether-hexane 1:2 at −25° C.), title compound C1 is obtained as a white crystallizate (27.5 g, 72%): Melting point 48–49° C.; TLC R$_f$=0.09 (diethyl ether/hexane 2:1); [α]$^{25}_D$=44.2 (c 1, chloroform); $^1$H-NMR (500 MHz, CDCl$_3$, δ): 0.85–1.07 (m, 12H), 1.57–1.65 (m, 1H), 1.79–2.00 (m, 3H), 2.07–2.27 (m, 6H), 2.62 (m, 1H), 2.75 (dd, 1H), 3.37 (s, 3H), 3.59 (t, 2H), 3.86 (s, 3H), 4.02 (m, 1H), 4.12 (t, 2H), 4.35 (m, 1H), 6.72 (dd, 1H), 6.75 (d, 1H), 6.81 (d, 1H) ppm.

D) Preparation of Compounds of Formula V

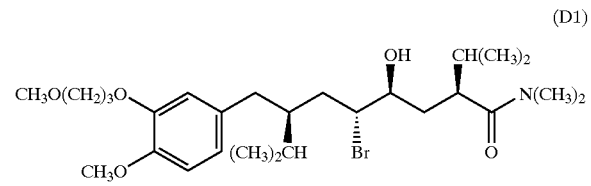

(D1)

EXAMPLE D1

A mixture of 6.52 g dimethylamine hydrochloride and 400 ml dichloromethane is cooled to −4° C., and 44.8 ml diethyl-aluminium chloride (1.8M in toluene) is added over a period of 10 minutes. The temperature is allowed to rise to 20° C., a solution of 20 g C1 in 80 ml dichloromethane is added and the mixture stirred for another 18 hours at 35° C. The reaction solution is cooled to 0° C. and then stirred in drop by drop to 800 ml 0.5N cold hydrochloric acid. The reaction mixture is extracted with tertiary butyl methyl ether (2×250 ml), and the resulting organic phases are consecutively washed with water (500 ml) and (concentrated aqueous saline solution (brine, 200 ml). The combined organic phases are dried over sodium sulfate, filtered and concentrated by evaporation. By means of flash chromatography (Sio$_2$ 60F/ethyl acetate/hexane 1:1), title compound D1 is obtained from the residue as a slightly yellowish oil (19.0 g, 68%): TLC R$_f$=0.16 (ethyl acetate/hexane 1:1); $^1$H-NMR (300 MHz, CDCl$_3$): δ 0.70–0.95 (m, 12H), 1.50–1.95 (m, 7H), 2.05 (m, 2H), 2.20 (m, 1H), 2.55–2.80 (m, 3H), 2.90 (s, 3H), 3.05 (s, 3H), 3.30 (s, 3H), 3.45 (m, 1H), 3.50 (t, 2H), 3.80 (s, 3H), 4.05 (t, 2H), 4.15 (m, 1H), 6.60–6.75 (m, 3H) ppm.

E) Preparation of Compounds of Formula VII

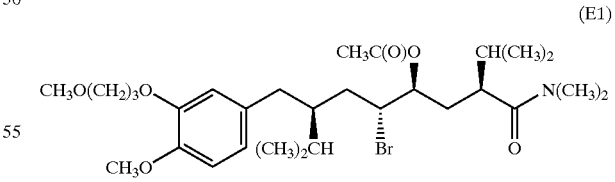

(E1)

EXAMPLE E1

A solution of 8.30 g D1 in 100 ml dichloromethane is mixed with 1.54 ml pyridine and cooled to 0° C. Then 1.73 ml acetic acid anhydride and 0.186 g 4-dimethylaminopyridine are added consecutively and the mixture is stirred for 18 hours at room temperature. The reaction mixture is poured onto 300 ml water and extracted with diethyl ether (2×300 ml). The organic phases are washed consecutively with water (300 ml), 5% aqueous sodium hydrogencarbonate solution (100 ml) and brine (100 ml). The combined organic phases are dried over sodium sulfate and concentrated by evaporation on a rotary evaporator. By means of flash chromatography ($SiO_2$ 60F/diethyl ether/hexane 1:1), title compound E1 is obtained from the residue as a colourless oil (7.67 g, 92%): TLC $R_f$=0.27 (ethyl acetate/hexane 1:1); $^1$H-NMR (300 MHz, $CDCl_3$): δ 0.80–1.00 (m, 12H), 1.65–2.20 (m, 9H), 2.10 (s, 3H), 2.35 (m, 1H), 2.50–2.65 (m, 2H), 3.00 (d, 6H), 3.40 (s, 3H), 3.60 (t, 2H), 3.85 (s, 3H), 4.15 (t, 2H), 4.10 (m, 1H), 4.70 (m, 1H), 6.70–6.85 (m, 3H) ppm.

F) Preparation of Compounds of Formula VI

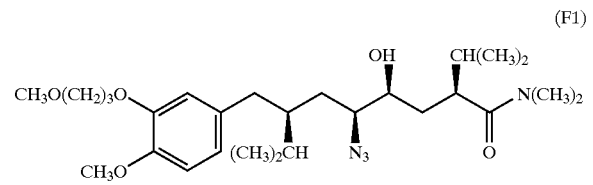

(F1)

EXAMPLE F1

A mixture of 0.10 g D1, 0.024 g sodium azide and 1 ml DMPU is stirred for 96 hours at 30° C. The reaction mixture is cooled to room temperature, 30 ml water added, and extraction carried out using diethyl ether (2×30 ml). The combined organic phases are washed with water (2×30 ml) and brine (1×10 ml), dried over sodium sulfate, filtered and concentrated by evaporation. By means of flash chromatography ($SiO_2$ 60F/ethyl acetate/hexane 1:1), title compound F1 is obtained from the residue as a colourless oil (27 mg, 29%): TLC $R_f$=0.14 (ethyl acetate/hexane 1:1); $^1$H-NMR (300 MHz, $CDCl_3$): δ 0.75–0.90 (m, 12H), 1.10–1.95 (m, 7H), 2.05 (m, 2H), 2.45 (d, 2H), 2.55 (d, 1H), 2.70 (m, 1H), 2.80–2.95 (m, 1H), 2.95 (s, 3H), 3.05 (s, 3H), 3.20–3.35 (m, 1H), 3.30 (s, 3H), 3.50 (t, 2H), 3.80 (s, 3H), 4.05 (t, 2H), 6.60–6.75 (m, 3H) ppm.

G) Preparation of Compounds of Formula VIII

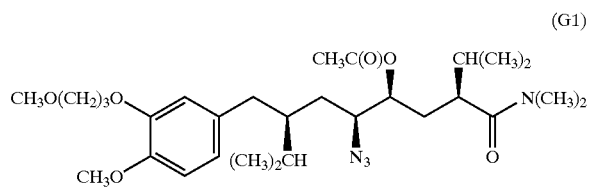

(G1)

EXAMPLE G1

A mixture of 1.17 g E1, 0.392 g lithium azide and 11.7 ml DMPU is stirred for 21 h at 60° C. The reaction mixture is cooled, and water (100 ml) added. Extraction is carried out using tertiary butyl methyl ether (3×80 ml) and the organic phases are then washed consecutively with water (3×100 ml), 5% aqueous sodium hydrogencarbonate solution (100 ml) and brine (100 ml). The combined organic phases are dried over sodium sulfate and concentrated by evaporation on a rotary evaporator. By means of flash chromatography ($SiO_2$ 60F/diethyl ether/hexane 3:1), title compound G1 is obtained from the residue as a colourless oil (0.83 g, 76%): TLC $R_f$=0.06 (diethyl ether/hexane 3:1); $^1$H-NMR (300 MHz, $CDCl_3$):-{ }-δ 0.80–1.00 (m, 12H), 1.15–1.20 (m, 1H), 1.40–2.20 (m, 8H), 2.05 (s, 3H), 2.40–2.60 (m, 3H), 3.00 (d, 6H), 3.05 (m, 1H), 3.40 (s, 3H), 3.60 (t, 2H), 3.90 (s, 3H), 4.15 (t, 2H), 4.75 (m, 1H), 6.70–6.85 (m, 3H) ppm.

H) Preparation of Compounds of Formula II

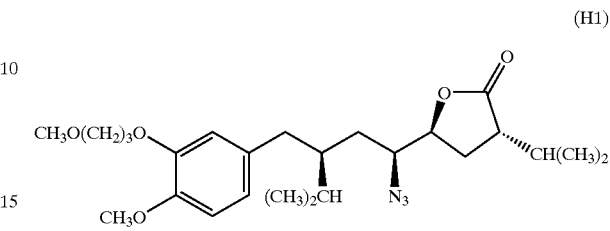

(H1)

EXAMPLE H1

A mixture of 70 mg F1, 2 ml toluene and 0.16 ml ethyl acetate is stirred for 4 hours at room temperature. The reaction mixture is cooled to room temperature, 5% aqueous sodium hydrogencarbonate solution (25 ml) is added, and extraction carried out using diethyl ether (2×20 ml). The combined organic phases are dried over sodium sulfate and concentrated by evaporation on a rotary evaporator. The dried residue corresponds to crude title compound H1 (quantitative); TLC $R_f$=0.41 (ethyl acetate/hexane 1:1); $^1$H-NMR (300 MHz, $CDCl_3$): δ 0.85–1.10 (m, 12H), 1.40 (m, 1H), 1.60–2.25 (m, 8H), 2.45 (m, 1H), 2.60. (m, 2H), 2.95 (m, 1H), 3.40 (s, 3H), 3.60 (t, 2H), 3.85 (s, 3H), 4.15. (t, 2H), 4.30 (m, 1H)), 6.70–6.85 (m, 3H) ppm.

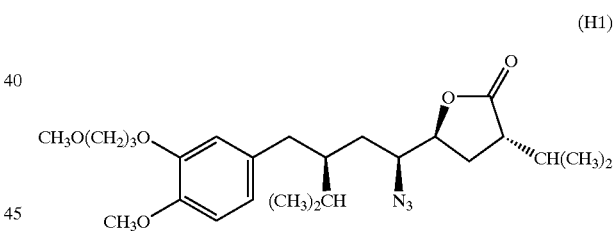

(H1)

EXAMPLE H2

A mixture of 55 mg G1, 38 mg p-toluenesulfonic acid hydrate and 1 ml methyl alcohol is stirred under reflux for 16 hours. The reaction mixture is cooled to room temperature, 5% aqueous sodium hydrogencarbonate solution (5 ml) is added, and extraction carried out using diethyl ether (2×10 ml). The combined organic phases are dried over sodium sulfate and concentrated by evaporation on a rotary evaporator. The dried residue corresponds to crude title compound H1 (0.043 g, 93%); TLC $R_f$=0.41 (ethyl acetate/hexane 1:1); $^1$H-NMR (300 MHz, $CDCl_3$): δ 0.85–1.10 (m, 12H), 1.40 (m, 1H), 1.60–2.25 (m, 8H), 2.45 (m, 1H), 2.60 (m, 2H), 2.95 (m, 1H), 3.40 (s, 3H), 3.60 (t, 2H), 3.85 (s, 3H), 4.15 (t, 2H), 4.30 (m, 1H)), 6.70–6.85 (m, 3H) ppm.

J) Preparation of Compounds of Formula III

EXAMPLE J1
Preparation of

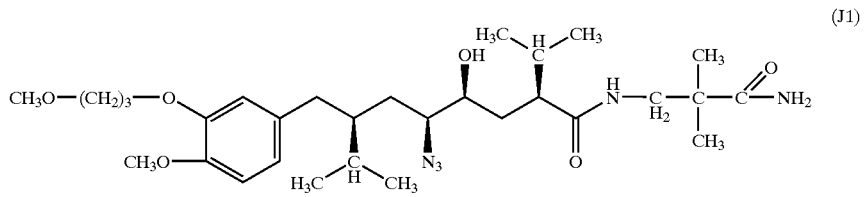

A mixture of 59.1 g H1, 41.82 g 3-amino-2,2-dimethylpropionamide, 2.28 g 2-hydroxypyridine in 59.1 ml triethylamine is stirred for 16 hours at 90° C. Then 33 ml triethylamine is distilled off over a period of 0.5 hours, and the residue is agitated for a further 8.5 hours at 90° C. The cooled reaction mixture is extracted between ethyl acetate (3×500 ml), saturated aqueous sodium hydrogencarbonate solution (1×500 ml) and saturated sodium chloride solution (1×500 ml). The combined organic phases are dried over 100 g sodium sulfate, filtered and concentrated on a rotary evaporator. The residue is dried and crude title compound F1 is obtained as an oil (78.4 g, quantitative) (HPLC assay: 88.5%): TLC $R_f$=0.13 (ethyl acetate—hexane 4:1); chromatographed sample: TLC $R_f$=0.13 (ethyl acetate/hexane 4:1); $^1$H-NMR (500 MHz, CDCl$_3$, δ): 0.85–0.96 (m, 12H), 1.23 (s, 6H), 1.30–1.40 (m, 1H), 1.53–1.80 (m, 5H), 1.82–1.93 (m, 1H), 2.06–2.14 (m, 3H), 2.45–2.57 (m, 2H), 2.87–2.92 (m, 1H), 3.13 (d, 1H), 3.32–3.52 (m, 3H), 3.36 (s, 3H), 3.59 (t, 2H), 3.84 (s, 3H), 4.12 (t, 2H), 5.51 (bs, 1H), 6.01 (bs, 1H), 6.43 (t, 1H), 6.72 (dd, 1H), 6.75 (d, 1H), 6.81 (d, 1H) ppm.

K) Hydrogenation of the Azide Group to Form Compounds of Formula I

EXAMPLE K1
Preparation of

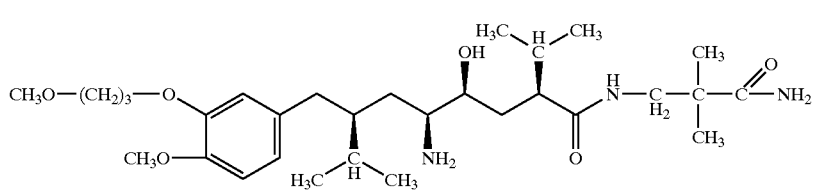

78.4 g (HPLC assay: 88.5%) F1 (crude) is hydrogenated for 3 hours in the presence of 3.92 g Pd/C$_5$% and 7.2 ml ethanol amine in 700 ml tert-butyl methyl ether at ambient temperature and 3.0 bar. The reaction mixture is filtered and the catalyst washed with 300 ml tert-butyl methyl ether. The filtrate is washed consecutively with 400 ml 2N NaOH and 400 ml brine. The aqueous phases are then extracted with tert-butyl methyl ether (2×400 ml). The combined organic phases are dried over 100 g sodium sulfate and concentrated by evaporation. The residue is mixed with 7.31 g fumaric acid and dissolved in 200 ml ethanol and filtered until clear. The filtrate is concentrated by evaporation to a total weight of 104 g and dissolved in 1.7 l acetonitrile at 35° C. The resulting solution is inoculated with 10 mg of title compound (hemifumarate) and agitated for 17 hours at ambient temperature. The suspension is cooled to 0° C. and filtered off by suction after 2 hours. The residue is washed with acetonitrile (3×200 ml) and then dried in a vacuum at 35° C.—he title compound K1 (hemifumarate) is obtained as white crystals (59.5 g, 81% in relation to J1):-{ }-$^1$H NMR (360 MHz, DMSO-d$_6$); δ 0.7–0.9 (m, 12H), 1.04 (s, 6H), 1.27 (m, 3H), 1.4–1.8 (m, 4H), 1.94 (m, 2H), 2.23 (m, 1H), 2.35 (dd, J=8.4, 8.0 Hz, 1H), 2.45 (m, 1H), 3.08 (m, 2H), 3.2–3.5 (m, 2H), 3.24 (s, 3H), 3.47 (t, J=6.4 Hz, 2H), 3.74 (s, 3H), 3.97 (t, J=6.4 Hz, 2H), 6.37 (s, 1H), 6.68 (dd, J=8.0, 2.0 Hz, 1H), 6.77 (d, J=6 Hz, 1H), 6.80 (bs, 1H), 6.83 (d, J=8 Hz, 1H), 7.13 (bs, 1H), 7.49 (t, J=6 Hz, 1H).

What is claimed is:

1. Compounds of formula IX,

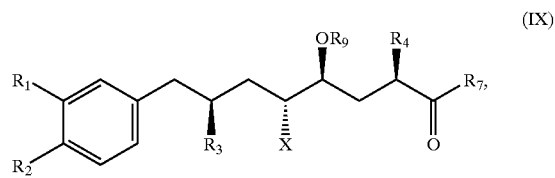

wherein

X is halogen, $R_1$ and $R_2$ are, independently of one another, H, $C_1$–$C_6$alkyl, $C_1$–$C_6$halogen-alkyl $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, $R_7$ is an amino group, and $R_9$ is a protecting group or hydrogen.

2. Compounds of formula IXa,

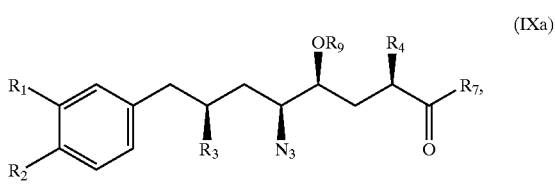

wherein $R_1$ and $R_2$ are, independently of one another, H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, $R_7$ is an amino group, and $R_9$ is a protecting group or hydrogen.

* * * * *